United States Patent [19]

Schempp

[11] 4,021,482
[45] May 3, 1977

[54] SULFINYL OR SULFONYL-1-CHLOROACRYLIC ACID AMIDES

[75] Inventor: Heinrich Schempp, Binningen, Switzerland

[73] Assignee: Ciba-Geigy Corporation, Ardsley, N.Y.

[22] Filed: July 25, 1974

[21] Appl. No.: 491,724

[30] Foreign Application Priority Data

Aug. 2, 1973 Switzerland .................... 11227/73

[52] U.S. Cl. .................. 260/561 S; 260/562 S; 424/320
[51] Int. Cl.² ............. C07C 143/16; C07C 145/02
[58] Field of Search .................... 260/561 S, 562 S

[56] References Cited

UNITED STATES PATENTS

| | | | |
|---|---|---|---|
| 3,022,344 | 2/1962 | Heininger et al. | 260/561 S X |
| 3,226,448 | 12/1965 | Gordon et al. | 260/649 F X |
| 3,437,685 | 4/1969 | Brust | 260/561 S X |
| 3,541,119 | 11/1970 | Richter et al. | 260/561 S X |
| 3,839,405 | 10/1974 | Dannals | 260/561 S X |
| 3,914,301 | 10/1975 | Miller et al. | 260/561 S |

FOREIGN PATENTS OR APPLICATIONS

| | | | |
|---|---|---|---|
| 1,157,026 | 7/1969 | United Kingdom | 260/561 S |
| 1,160,454 | 8/1969 | United Kingdom | 260/561 S |

*Primary Examiner*—Allen B. Curtis
*Attorney, Agent, or Firm*—Harry Falber

[57] ABSTRACT

1-Chloroacrylic acid amide derivatives of formula I

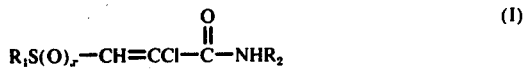

wherein
$R_1$ represents $C_1$–$C_4$-alkyl,
$R_2$ represents $C_1$–$C_8$-alkyl, or a cycloalkyl bound directly or by way of an alkylene bridge member, or a benzyl or phenyl radical which is unsubstituted or at most tri-substituted in the aromatic nucleus, and
$x$ represents the number 1 or 2, are effective agents for the control of microorganisms. They may also be used as active substances in seed dressing agents.

6 Claims, No Drawings

SULFINYL OR SULFONYL-1-CHLOROACRYLIC ACID AMIDES

The present invention relates to microbicidal agents containing 1-chloroacrylic acid amide derivatives, to processes for preparing these active substances, as well as to their use for the control of various microorganisms. The invention relates also to the new 1-chloroacrylic acid amide derivatives, used as microbicidal active substances, of formula I $$R_1S(O)_x-CH=CCl-\underset{\underset{O}{\|}}{C}-NHR_2 \quad (I)$$

wherein
$R_1$ represents $C_1-C_4$-alkyl,
$R_2$ represents $C_1-C_8$-alkyl, or a cycloalkyl bound directly or by way of an alkylene bridge member, or a benzyl or phenyl radical which is unsubstituted or at most tri-substituted in the aromatic nucleus, and
X represents the number 1 or 2.

Alkyl radicals $R_1$ and $R_2$ are straight-chain or branched-chain hydrocarbon radicals, preferably ones having 1 to 4 carbon atoms, such as the methyl, ethyl, n-propyl, isopropyl, n-butyl, isobutyl, sec.butyl or tert.butyl radical. By cycloalkyl in the general formula I are meant the following radicals: cyclopropyl, cyclobutyl, cyclopentyl and cyclohexyl. The alkylene bridge for cycloalkyl radicals is preferably the methylene group. Benzyl as well as phenyl can be up to tri-substituted, or they can be unsubstituted. Substituents can be: methyl, ethyl, halogen, nitro, haloalkyl — preferably trifluoromethyl — or $C_1-C_3$-alkoxy.

The new 1-chloroacrylic acid amide derivatives of formula I are obtained by reaction of a 1,2-dichloroacrylic acid amide of formula II $$ClCH=CCl-\underset{\underset{O}{\|}}{C}-NHR_2 \quad (II)$$

in the presence of an acid-binding agent, with a compound of formula III $$R_1SH \quad (III)$$

or with the alkali salt thereof, and conversion of the resulting thio compound with one or two equivalents of an oxidising agent into the corresponding sulphinyl or sulphonyl compound.

Suitable acid-binding agents are inorganic bases such as hydroxides and carbonates of alkali metals and alkaline-earth metals, and organic bases such as trialkylamines, pyridine and pyridine bases. Alkali alcoholates dissolved in the corresponding alcohol are preferably used for the reaction. The reaction temperatures are between 0° and 80°.

Oxidation is effected preferably by means of peroxy acids, such as peroxyacetic acid or m-chloroperoxybenzoic acid, or by means of hydrogen peroxide in glacial acetic acid, in the presence of a solvent or diluent inert to the reactants. The following are, for example, suitable: aliphatic, aromatic or halogenated hydrocarbons such as benzene, toluene, xylenes, chlorobenzene, methylene chloride and chloroform; ketones such as acetone or methyl ethyl ketone; nitriles such as acetonitrile, as well as mixtures of such solvents with each other. The reaction temperatures are between −20° and +60° C.

The starting materials of formula II are in some cases known, or they can be prepared by processes known per se, for example, by reaction of a dichloroacrylic acid halide with an amine of the formula $H_2NR_2$.

The following examples illustrate the preparation of the compounds of the invention; temperatures are given in degrees Centigrade.

EXAMPLE 1

Preparation of an intermediate

A. A solution of 7.85 g of sodium methylate and 7 g of methyl mercaptan in 120 ml of methanol is added dropwise at 25° to 35°, with stirring, to a solution of 35 g of 1,2-dichloroacrylic acid-4'-chloro-2'-methyl-anilide in 200 ml of methanol Stirring is continued for 2 hours at 50° to 60°, and the reaction mixture is then concentrated by evaporation. The residue is taken up in methylene chloride and washed free from salt with water. The methylene chloride phase is dried, concentrated by evaporation and the residue is recrystallised from methanol. There is obtained 25.3 g of 1-chloro-2-methylthioacrylic acid-4'-chloro-2'-methyl-anilide having a melting point of 81°–82°.

B. A solution of 33.1 g of 40% peroxyacetic acid in 50 ml of methylene chloride is added dropwise at −5° to 0°, with stirring, to a solution of 20 g of 1-chloro-2-methylthioacrylic acid-4'-chloro-2'-methyl-anilide in 150 ml of methylene chloride. The reaction mixture is further stirred for two hours down to room temperature; it is then washed neutral with water and sodium bicarbonate solution, the methylene chloride phase is dried and the solvent is evaporated off. The residue is purified by repeated trituration with diethyl ether to obtain 19 g of 1-chloro-2-methylsulphonylacrylic acid-4'-chloro-2'-methyl-anilide, M.P. 152° (Compound 1).

EXAMPLE 2

A solution of 19.6 g of 40% peroxyacetic acid in 50 ml of methylene chloride is added dropwise at −10°, with stirring, to 24 g of 1-chloro-2-methylthioacrylic acid-cyclohexylamide dissolved in 200 ml of methylene chloride. The reaction mixture is stirred for a further hour up to 0°, and for a further two hours up to room temperature; it is then washed until neutral with water and sodium bicarbonate solution, and the organic phase is dried, and concentrated by evaporation. The residue is triturated several times with diethyl ether. There is obtained 18 g of 1-chloro-2-methylsulphinylacrylic acid-cyclohexylamide having a melting point of 86° to 88° (Compound 2).

Table a $$R_1SO-CH=CCl-\underset{\underset{O}{\|}}{C}-NHR_2$$

| Comp. No. | $R_1$ | $R_2$ | Melting point |
|---|---|---|---|
| 3 | —CH$_3$ | 2,4-dichlorophenyl | 156°–158° |
| 4 | —CH$_3$ | 4-chloro-2-trifluoromethylphenyl | 162°–163° |

Table a-continued $$R_1SO-CH=CCl-\overset{\overset{O}{\|}}{C}-NHR_2$$

| Comp. No. | R₁ | R₂ | Melting point |
|---|---|---|---|
| 5 | —CH₃ | phenyl | 125°–126° |
| 6 | —CH₃ | 4-chlorophenyl | 137°–139° |
| 7 | —CH₃ | 2,6-dimethylphenyl | 126°–127° |
| 8 | —CH₃ | —C₃H₇(iso) | 87°–89° |
| 9 | —CH₃ | 2-methoxyphenyl | 77° |
| 10 | —CH₃ | —CH(CH₃)—C(CH₃)₂ | 120° |
| 11 | —CH₃ | —CH₂—cyclohexyl | 82° |
| 12 | —CH₃ | —C₄H₉(iso) | — |
| 12 a | —CH₃ | 2-methyl-4-chlorophenyl | 141–143° |

Table b $$R_1SO_2-CH=CCl-\overset{\overset{O}{\|}}{C}-NHR_2$$

| Comp. No. | R₁ | R₂ | Melting point |
|---|---|---|---|
| 13 | —CH₃ | phenyl | 116°–117° |
| 14 | —CH₃ | 2-CF₃-4-Cl-phenyl | 165°–166° |
| 15 | —CH₃ | 3,5-dichlorophenyl | 157°–158° |
| 16 | —CH₃ | 3-CF₃-phenyl | 111°–112° |
| 17 | —CH₃ | cyclopentyl | 94°–95° |
| 18 | —CH₃ | —CH₂—phenyl | 92°–94° |
| 19 | —CH₃ | 4-chlorophenyl | 144° |

Table b-continued $$R_1SO_2-CH=CCl-\overset{\overset{O}{\|}}{C}-NHR_2$$

| Comp. No. | R₁ | R₂ | Melting point |
|---|---|---|---|
| 20 | —CH₃ | 4-fluorophenyl | 123° |
| 21 | —CH₃ | cyclohexyl | 90°–92° |
| 22 | —CH₃ | 2-fluorophenyl | 95°–97° |
| 23 | —CH₃ | —C₃H₇(iso) | 84° |
| 24 | —CH₃ | 3-fluorophenyl | 111°–112° |
| 25 | —CH₃ | —C₃H₇(n) | 78°–79° |
| 26 | —CH₃ | cyclopropyl | 111°–112° |
| 27 | —CH₃ | —C₄H₉(tert) | 94°–96° |
| 28 | —CH₃ | —C₄H₉(iso) | 83°–84° |
| 29 | —CH₃ | 2,6-dimethylphenyl | 146°–147° |
| 30 | —CH₃ | 2-CF₃-phenyl | 88° |
| 31 | —CH₃ | 2-methyl-6-chlorophenyl | 140° |
| 32 | —CH₃ | 2-methoxyphenyl | 134° |
| 33 | —CH₃ | 2-chlorophenyl | 90° |
| 34 | —CH₃ | —CH[CH(CH₃)₂]₂ | 80° |
| 35 | —CH₃ | —CH₂—C(CH₃)₃ | 77° |
| 36 | —CH₃ | —CH(CH₃)—C(CH₃)₃ | semicrystalline |
| 37 | —CH₃ | —CH₂—cyclohexyl | 111° |
| 38 | —CH₃ | 2-isopropylphenyl | 118° |

Table b-continued

| Comp. No. | R₁ | R₂ | Melting point |
|---|---|---|---|
| 39 | —CH₃ | —C₆H₄—NO₂ | 136° |
| 40 | —CH₃ | —C₆H₃(Cl)—Cl | 154° |
| 41 | —CH₃ | —C₆H₄—CH₃ | 82° |
| 42 | —CH₃ | —C₆H₂(CH₃)(CH₃)—CH₃ | 176° |

The compounds of formula I possess microbicidal properties and they can be used for the control of various microorganisms. Compounds of particular importance are those embraced by formula Ia $$CH_3-S(O)_x-CH = CCl - CONHR'_2 \quad (Ia)$$

wherein X represents 1 or 2, and R₂' stands for C₃–C₄-alkyl or for a phenyl radical which is unsubstituted or at most di-substituted with Cl, Br and/or CF₃.

Very effective compounds are, for example:
1-chloro-2-methylsulphinyl-acrylic acid-3'-trifluoromethyl-4'-chloroanilide,
1-chloro-2-methylsulphonyl-acrylic acid-isopropylamide,
1-chloro-2-methylsulphonyl-acrylic acid-n-propylamide,
1-chloro-2-methylsulphonyl-acrylic acid-anilide.

Such α-chloroacrylic acid amides of formula I are fungicides and are particularly valuable for the control of phytopathogenic fungi. Infestations by species of the classes Phycomycetes (Oomycetales), e.g. *Phytophthora infestans, Plasmopara viticola;* Ascomycetes, e.g. *Erysiphe cichoracearum, Erysiphe graminis, Podosphaera leucotricha* and *Venturia inaequalis;* Basidiomycetes, e.g. *Uromyces phaseoli, Puccinia graminis tritici, Ustilage nuda* and *Tilletia caries; Fungi imperfecti,* e.g. *Botryis cinerea, Piricularia oryzae, Septoria apicola, Penicillium digitatum* and *Alternaria solani,* can be prevented or localised by the application of these active substances. The compounds of formulae I and Ia are however effective, in particular, against species of fungi which infest parts of the plant that are below the soil, such as roots, the base of stalks, seeds, tubers and seedlings, and other plant parts serving to promote propagation. Among these are, for example, the following: *Pythium debaryanum, Ophiobolum graminis, Tilletia caries, Rhizoctonia solani, Fusarium oxysporum, Fusarium nivale* and *Verticillium albo-atrum.* With the compounds of formula I and particularly with those of formula Ia, it is possible to treat according to the invention also all species of seed, seedlings and cuttings, e.g. of wheat, rye, barley, oats, maize, rice, cotton, sugar beet, vegetables, seed potatoes, groundnuts or flower bulbs, and to effectively protect them against fungus infestation. This renders possible the control of practically all phytopathogenic fungi and spores thereof which otherwise damage the seed present in the soil and lead to serious plant diseases. An active substance having in this respect a particularly good action is 1-chloro-2-methylsulphonyl-acrylic acid isobutylamide. It is especially suitable for dressing, for example, the seed of sugar beet and cotton.

The following tests were carried out to determine the phytofungicidal action.

Dressing-agent action a. Action as dressing agent against *Fusarium nivale* and *Helminthosporium gramineum*

Wheat is artificially infested with the respective test organism; 500 ppm of active substance in the form of a dispersion is then evenly distributed by shaking over the grains of wheat. The grains are afterwards laid out on a culture in Petri dishes and allowed to stand for 3 days at 20° C to 22° C. The mycelium growth on the grains and around them on the culture is then evaluated in percent.

b. Action as dressing agent against *Tilletia caries*

Dry sieved soil is placed into Petri dishes; there is then added to the soil an aqueous suspension containing the active substance at a concentration of 500 ppm. A minute amount of spores of Tilletia caries is then placed in the centre of each dish. The incubation is for 7 days at 12° C. An evaluation of the smut spores is afterwards made.

In these tests, the compounds of formula I according to the invention exhibited an excellent action. To be particularly emphasised as soil fungicides are the compounds Nos. 3 – 6, 8 and also 23, 25, 27 and 28. They prevent fungus infestation to the extent of over 80% in comparison with the untreated control dishes.

The agents according to the invention are prepared in a manner known per se by the intimate mixing and grinding of active substances of the general formula I with suitable carriers, optionally with the addition of dispersion agents or solvents which are inert to the active substances. The active substances can be obtained and employed in the following forms:
solid preparations:
  dusts, scattering agents, granulates, coated granulates, impregnated granulates and homogeneous granulates;
water-dispersible active-substance concentrates:
  wettable powders, pastes and emulsions;
liquid preparations:
  solutions.

Other biocidal active substances may be added to the described agents according to the invention. Thus, in addition to the mentioned compounds of the general formula I, the new agents can contain for the broadening of the range of action, for example, insecticides, fungicides, bactericides, fungistatics, bacteriostatics or nematocides. The agents of the invention can also contain fertilisers, trace elements, etc.

Preparations of the new active substances of the general formula I are given in the following. Parts are expressed as parts by weight.
Granulate:

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3 – 0.8 mm).

The active substance is mixed with epichlorhydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder:

The following constituents are used for the preparation of (a) a 40%, (b) and (c) a 25% and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance No. 28,
4.5 parts of calcium lignin sulphonate
1.9 parts of Champagne chalk/hydroxyethyl cellulose mixture (1:1),
1.5 parts of sodium dibutyl naphthalene sulphonate,
19.1 parts of silicic acid,
19.5 parts of Champagne chalk,
28.1 parts of kaolin.

(c)

25 parts of active substance No. 4,
2.5 parts of isooctylphenoxy-polyoxyethylene-ethanol
1.7 parts of Champagne chalk/hydroxyethyl cellulose mixture (1:1),
8.3 parts of sodium aluminum silicate,
16.5 parts of kieselguhr,
46 parts of kaolin.

(d)

10 parts of active substance No. 25
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:

(a) 10 parts of active substance No. 4, 3.4 parts of epoxidised vegetable oil,
13.4 parts of a combination emulsifier consisting of fatty alcohol polyglycol ether and alkylarylsulphonate calcium salt,
40 parts of dimethylformamide,
33.2 parts of xylene.

(b)

25 parts of active substance,
2.5 parts of epoxidised vegetable oil,
10 parts of an alkylarylsulphonate/fatty alcoholpolyglycol ether mixture,
5 parts of dimethylformamide,
57.5 parts of xylene.

Emulsions of any desired concentration can be prepared from these concentrates by dilution with water.

Dry dressing agent 20 parts of active substance No. 28,
1 part of paraffin oil,
79 parts of talcum.

Wet dressing agent 23 parts of active substance No. 28,
1.65 parts of alkarylpolyglycol ether (emulsifier),
1.65 parts of $NaHSO_4 \cdot H_2O$, finely ground,
73.7 parts of diethylene glycol monoethyl ether acetate.

Furthermore, the active substances of formulae I and Ia can be used in the form of solutions, emulsions and suspensions for the preservation of organic materials, such as wood, paper, plastics, coating agents, etc., as well as disinfectants, e.g. in soaps, detergents and rinsing baths.

The antimicrobics mentioned are thus suitable for use as preservatives and disinfectants for commercial products of all kinds, such as glues, binders, coating agents, textile auxiliaries or finishing agents, dyeing and printing pastes and similar preparations based on organic dyestuffs and pigments, also such products containing as additives casein or other organic compounds.

The compounds of the invention can be used as preservatives also in the cellulose and paper industry for, inter alia, the prevention of the known formation of mucilage, caused by microorganisms, in the equipment used for making paper.

The action of the compounds of formula I may be utilised also for imparting to plastics a preserving and disinfecting finish, such as is desired, for instance, for consumer goods of all kinds, such as for foot mats, foot gratings in swimming baths, wall coverings, etc. By incorporation of the said compounds into the appropriate wax compositions and polishing waxes, there are obtained floor and furniture preserving agents having a disinfecting action.

On account of better solubility in organic solvents, the active substances are also very suitable for application from non-aqueous media. Organic solvents are, for example, trichloroethylene, propylene glycol, methoxyethanol and dimethylformamide, to which can also be added dispersing agents and/or other auxiliaries.

Depending on the purpose of application, the content of active substances of the present invention can be between 0.1 and 50 g, preferably between 1 and 30 g of active substance per liter of treatment liquid.

By combination of the compounds of the invention with interface-active substances, there are obtained detergents and cleansing agents having antibacterial or antimycotic action, such as is desirable in the foodstuff industry, breweries, dairies and slaughterhouses.

The detergents and cleansing agents may be in any desired liquid, pulp-like, solid, flaky or granular form. The compounds of the invention can be incorporated both into anion-active compounds (such as soaps) and into cation-active surfactants or mixtures of various surfactants. The content of active substance in detergents and cleansing agents is in general 0.01 to 5%, in most cases 0.1 to 3%.

For disinfectants and preservatives, the compounds can also be used in combination with known antimicrobial agents.

Gradient-plate test for determining antimicrobial effectiveness

[Method: W. Szybalski et al., J. Bact. 64, 489 (1952)]
30 cm³ of a liquid agar solution containing 100 ppm of test substance is poured on to a wedge-shaped layer of agar (30 cm³) in a flat 100 × 100 × 15 mm glass vessel. During cooling of the solution, the active substance partially diffuses into the lower agar layer. There is thus obtained a concentration gradient in the direction of the greatest thickness of the lower agar layer.

Standardised suspensions of bacteria or fungi of the following species are applied, parallel to the concentration gradient, onto the surface of the combined layers of agar:

| | |
|---|---|
| staphylococcus aureus | Erwinia salicis |
| Streptococcus faecalis | Escherichia coli |
| Bacillus subtilis | Proteus vulgaris |
| Candida albicans | Pseudomonas solanacearum |
| Trichophyton mentagrophytes | Pseudomonas lachrymans |
| Aspergillus elegans | Xanthomonas vesicatoria |

After incubation of the cultures for 24 hours at 37° C (bacteria) or 72 hours at 28° C (fungi), a complete prevention of microbial growth was effected by, in particular, the compounds Nos. 13, 14, 23, 25, 34, 35 and 36 with 100 ppm or less.

What we claim is:

1. Chloroacrylic acid amide derivative of formula Ia

wherein X represents 1 or 2, and $R_2'$ stands for $C_3$-$C_4$-alkyl, or for an unsubstituted phenyl radical or a phenyl radical at most di-substituted with Cl, Br or $CF_3$.

2. The compound according to claim 1 of the formula

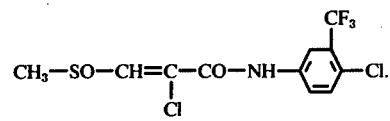

3. The compound according to claim 1 of the formula

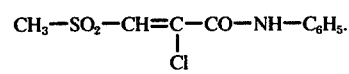

4. The compound according to claim 1 of the formula

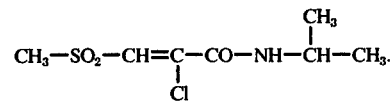

5. The compound according to claim 1 of the formula

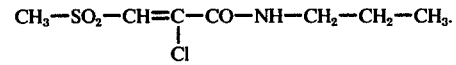

6. The compound according to claim 1 of the formula

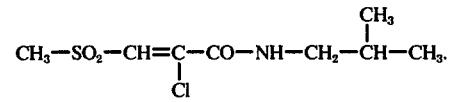

* * * * *